United States Patent [19]

Ecke, Jr.

[11] Plant 4,238

[45] Apr. 11, 1978

[54] POINSETTIA PLANT

[76] Inventor: Paul Ecke, Jr., P.O. Box 488, Encinitas, Calif. 92024

[21] Appl. No.: 720,366

[22] Filed: Sep. 3, 1976

[51] Int. Cl.[2] ..... A01H 5/00
[52] U.S. Cl. ..... Plt./86
[58] Field of Search ..... Plt./86

[56] References Cited

U.S. PATENT DOCUMENTS

P.P. 3,394 8/1973 Ecke ..... Plt./86

*Primary Examiner*—Robert E. Bagwill
*Attorney, Agent, or Firm*—Frank B. Robb

[57] ABSTRACT

A Poinsettia plant characterized by its smooth, erect, non-drooping bracts.

2 Drawing Figures

1

The present invention relates to a new and distinct variety of Poinsettia plant, which I designate as "Annette Hegg Super Star", botanically known as *Euphorbia pulcherrima,* which was discovered by me as a Tetraploid sport of the Poinsettia variety known as "Annette Hegg Maxi" (U.S. Plant Pat. No. 3,394), said discovery having been made by me in one of my greenhouses located at Encinitas, Calif.

I have long been carrying on a program of hybridization at my greenhouses at Encinitas, with various poinsettia varieties, and at the time of my discovery aforesaid, I was growing many of the plants of the patent variety "Annette Hegg Maxi".

As will be understood, I was necessarily observing very closely the growth of these particular plants, and during these observations, my attention was attracted to one particular plant of "Annette Hegg Maxi" group which appeared to substantially differ from that variety in that the bract being smoother and very erect had little tendency to droop.

Since I was interested in observing these plants for sports, I particularly selected this one and carefully preserved the same and kept it under close observation.

Subsequently I asexually reproduced the sport by vegetative cuttings taken therefrom, and planted in my greenhouses at Encinitas, Calif.

The aforementioned distinguishing characteristics and features of this tetraploid sport originally recognized by me following continued observations of the original sport and its progeny derived from the vegetative cuttings aforesaid, including other differences subsequently noted during continued observations, came true and remained stable. I am thus convinced that the sport is a valuable new and distinct variety for commercial purposes as evidenced by the following unique combination or characteristics which appear to be outstanding and which distinguishes it from other varieties of which I am aware:

(1) A resemblance to the variety known as "Annette Hegg Maxi" (U.S. Plant Pat. No. 3,394);

(2) The uniform and fast rooting habit which is comparable to "Annette Hegg" (U.S. Plant Pat. No. 2,962);

(3) Fewer stems and bracts than "Annette Hegg";

(4) Large and fleshy leaves of a dark green color like those of "Annette Hegg Maxi";

(5) The good bright red bract color, with some bluish tones like those of "Annette Hegg Maxi";

(6) The more rounded bract form than "Annette Hegg";

2

(7) Very large and prominent cyathea similar to "Annette Hegg Maxi";

(8) Long lasting plant qualities; and (9) Smooth very erect bracts which have little tendency to droop as does "Annette Hegg Maxi".

The accompanying drawing showing a typical specimen plant of my new poinsettia variety depicted in color as nearly true as is reasonably possible to make a color illustration of this character, is representative of such new variety.

While the details of my new poinsettia variety are quite similar in many respects to those described in U.S. Plant Pat. No. 3,394, reference to the same being available, the following brief description of the new sport is provided for convenience with color terminology in accordance with Wilson's Horticultural Colour Chart, except as to those general color terms which have ordinary dictionary significance, and thus are obvious:

Parentage: Tetraploid sport of "Annette Hegg Maxi" (U.S. Plant Pat. No. 3,394).

Propagation: Holds its distinguishing characteristics through succeeding propagations by vegetative cuttings.

Locality where grown and observed: Encinitas, Calif.

Form: Very short-growing with very thick stems; compact.

Habit of growth: Self-branching, but does not produce as many stems or bracts as "Annette Hegg".

Rooting habit: Very uniform; very fast.

Blooming habit: Same as "Annette Hegg Maxi".

Blooming season: Same as "Annette Hegg Maxi".

Foliage: Larger and fleshier than "Annette Hegg" and more rounded in form.

*Color.*—Near Ivy Green, Plate 0001060/1; much darker in color than leaves of "Annette Hegg".

Bracts:

*Shape.*—More rounded than bracts of "Annette Hegg" and more erect with less tendency to droop.

*Color.*—Good bright red, near Blood Red, Plate 820/3 with some bluish tones.

Flowers (Cyathea): Very large and prominent.

Reproductive organs:

*Stamens.*—Quite numerous. Color — Near Currant Red, Plate 821/2.

*Pollen.*—Color — Canary Yellow, Plate 2.

*Styles.*—Color — Near Blood Red, Plate 820.

*Ovaries.*—Color — Near Scheele's Green, Plate 860/1.

*Nectar cups.*—Color — Near Lemon Yellow, Plate 4/1.

General observations: While this new tetraploid sport generally resembles the parent variety "Annette Hegg Maxi" in some respects, it particularly differs therefrom by having smooth bracts which are very erect, and have little tendency to droop.

I claim:

1. A new and distinct variety of Poinsettia plant, substantially as herein shown and described, characterized particularly as to novelty by the unique combination of a general resemblance to the variety known as "Annette Hegg Maxi", (U.S. Plant Pat. No. 3,394), the smooth bracts being very erect and having little tendency to droop.

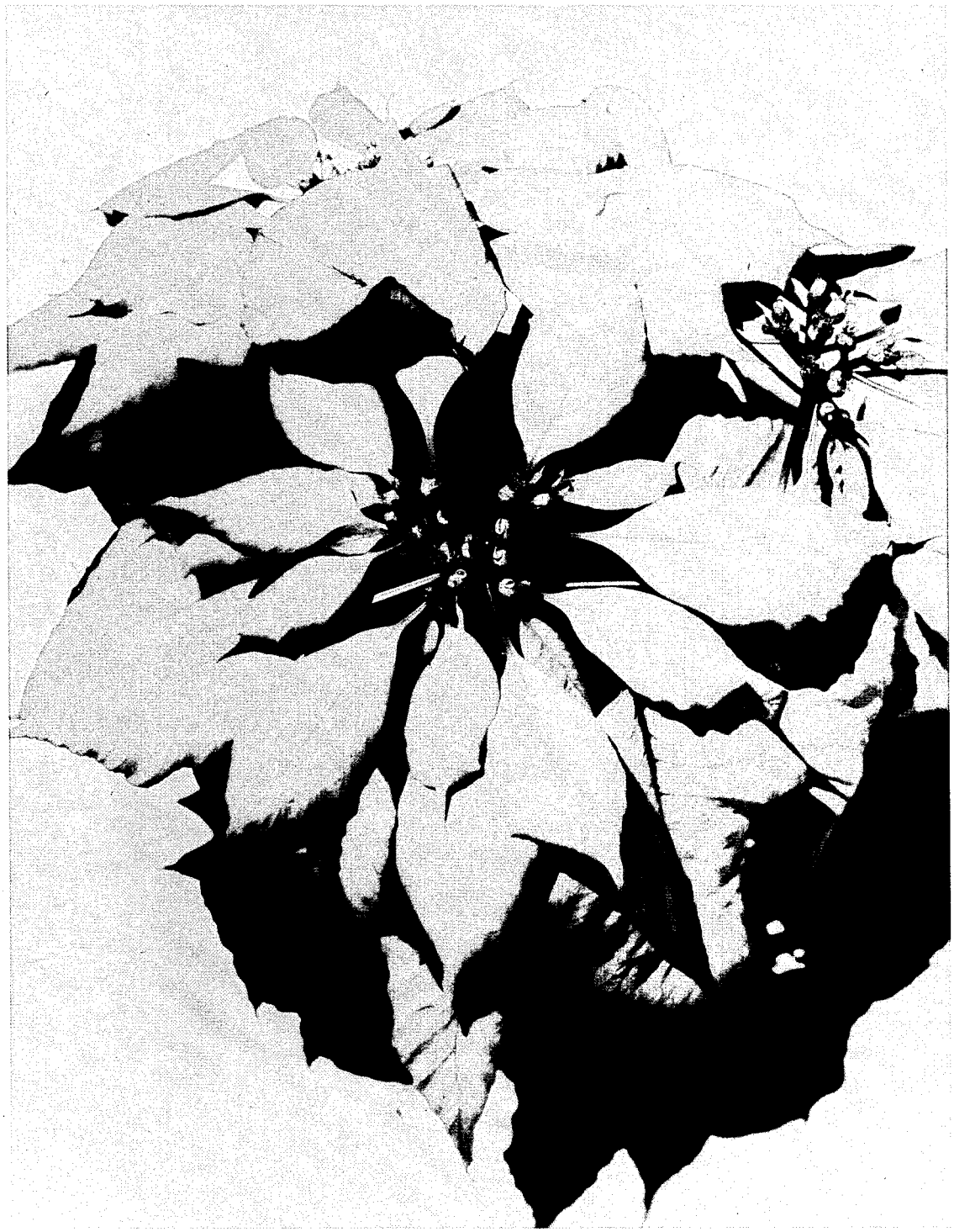

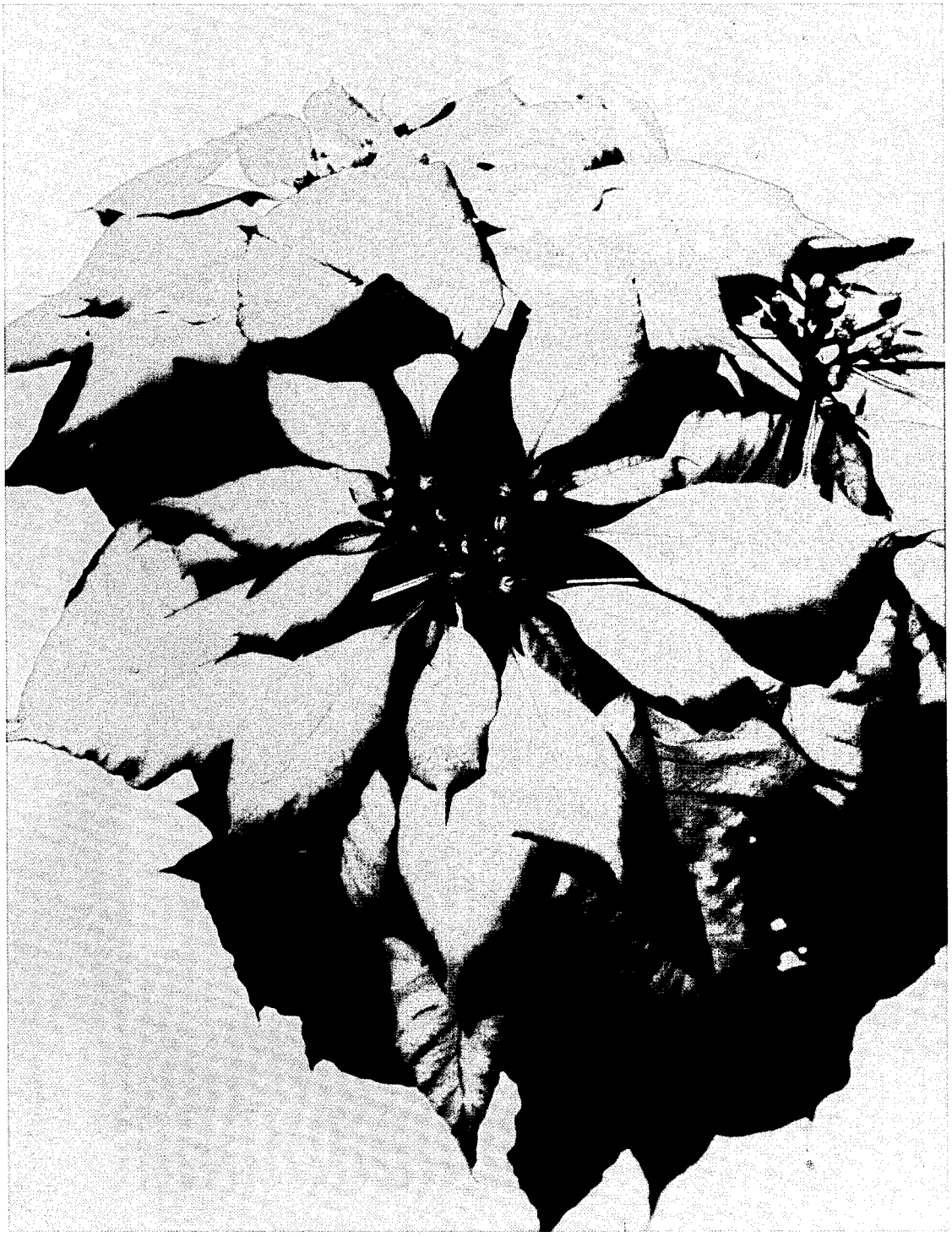

* * * * *